United States Patent
Ko et al.

(10) Patent No.: US 11,554,091 B2
(45) Date of Patent: Jan. 17, 2023

(54) COMPOSITION FOR ENHANCING SKIN ELASTICITY OR IMPROVING SKIN WRINKLES COMPRISING HEPTAHYDROXYFLAVAN AS AN EFFECTIVE INGREDIENT

(71) Applicant: AMOREPACIFIC CORPORATION, Seoul (KR)

(72) Inventors: Jaeyoung Ko, Yongin-si (KR); Mi Suk Yang, Yongin-si (KR); Eunjung Lee, Yongin-si (KR); Yong Jin Kim, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 194 days.

(21) Appl. No.: 16/908,099

(22) Filed: Jun. 22, 2020

(65) Prior Publication Data

US 2021/0000726 A1    Jan. 7, 2021

(30) Foreign Application Priority Data

Jul. 2, 2019 (KR) ........................ 10-2019-0079304

(51) Int. Cl.
*A61K 8/49* (2006.01)
*A61Q 19/08* (2006.01)
*A23L 29/00* (2016.01)

(52) U.S. Cl.
CPC ............ *A61K 8/498* (2013.01); *A23L 29/035* (2016.08); *A61Q 19/08* (2013.01)

(58) Field of Classification Search
None
See application file for complete search history.

(56) References Cited

U.S. PATENT DOCUMENTS

| | | |
|---|---|---|
| 10,137,070 B2 | 11/2018 | Park |
| 2006/0110352 A1 | 5/2006 | Milbradt et al. |
| 2011/0311661 A1* | 12/2011 | Behr ................ A61P 29/00 424/770 |

FOREIGN PATENT DOCUMENTS

| | | | |
|---|---|---|---|
| CN | 103417425 | A | 12/2013 |
| JP | 2006-111627 | A | 4/2006 |
| JP | 5139629 | B2 | 2/2013 |
| JP | 2016-193857 | A | 11/2016 |
| KR | 10-2012-0095296 | A | 8/2012 |
| KR | 20150082003 | A * | 7/2015 |
| KR | 10-1662779 | B1 | 9/2016 |
| KR | 10-1702389 | B1 | 2/2017 |
| KR | 10-1710194 | B1 | 2/2017 |
| WO | 2014/109629 | A1 | 7/2014 |

OTHER PUBLICATIONS

English translation of KR20150082003A (Year: 2015).*
Nagendra Prasad et al., "Phytochemicals and Antioxidant Capacity from Nypa fruticans Wurmb. Fruit," Evidence-Based Complementary and Alternative Medicine, 2013, vol. 2013, pp. 1-9.
Gi-Sang Bae et al., "The Anti-inflammatory Effect of Nypa fruticans Wurmb. Fruit on Lipopolysaccharide-induced Inflammatory response on RAW 264.7 cells," The Korea journal of herbology, 2016, vol. 31, No. 5, pp. 79-84.
Madhurima Bakshi et al., "Antimicrobial Potential of Leaf Extracts of Ten Mangrove Species from Indian Sundarban," International Journal of Pharma and Bio Sciences, 2014, vol. 5, No. 1, pp. 294-304.

* cited by examiner

*Primary Examiner* — Nicole P Babson
(74) *Attorney, Agent, or Firm* — Merchant & Gould P.C.

(57) ABSTRACT

Heptahydroxyflavan or a salt, isomer, hydrate or solvate thereof, which is an active ingredient of the present disclosure, can enhance skin elasticity and improve skin wrinkles by inhibiting the activity of MMP-1. In addition, the heptahydroxyflavan or a salt, isomer, hydrate or solvate thereof, which is an active ingredient of the present disclosure, can be used in various compositions such as cosmetics, health functional foods, etc. because it is safe with no cytotoxicity.

6 Claims, 4 Drawing Sheets

COMPOSITION FOR ENHANCING SKIN ELASTICITY OR IMPROVING SKIN WRINKLES COMPRISING HEPTAHYDROXYFLAVAN AS AN EFFECTIVE INGREDIENT

CROSS-REFERENCE TO RELATED APPLICATION

This application claims the priority of Korean Patent Application No. 10-2019-0079304, filed on Jul. 2, 2019, and all the benefits accruing therefrom under 35 U.S.C. § 119, the contents of which in their entirety are herein incorporated by reference.

BACKGROUND

1. Field

Disclosed in the present disclosure is a composition for enhancing skin elasticity or improving skin wrinkles.

2. Description of the Related Art

Although all people want to evade aging, a method for perfectly preventing biological aging is not known yet. The activity and regeneration ability of skin cells decline with age, leading to skin aging involving skin pigmentation such as freckles, lentigines, age spots, etc. and decreased skin elasticity. These phenomena occur differently among people depending on environmental factors such as environmental pollution and UV as well as intrinsic and genetic factors.

MMPs (matrix metalloproteinases) are calcium-dependent metalloproteinases containing zinc in the active site. They are secreted in vivo in the form of latent zymogens and is activated enzymatically through structural modification. MMPs are activated as the amino terminal site is cleaved. The activity of the activated MMPs is regulated by inhibitors such as 2-macroglobulin or TIMPs (tissue inhibitors of metalloproteinases). Many skin cells including keratinocytes, fibroblasts, etc. secrete MMPs. The MMP family can be classified into various subgroups depending on structural and functional characteristics. Among them, MMP-1, also known as interstitial collagenase, is a protein important in wound healing, tissue regeneration and reconstitution. Upon exposure to UV, MMP-1 is produced in larger quantities in the body than usual and induces skin wrinkles and decreased skin elasticity by binding to and cleaving collagen.

The inventors of the present disclosure have sought for a method for enhancing skin elasticity and improving skin wrinkles. In doing so, they have identified that heptahydroxyflavan is effective in enhancing skin elasticity and improving skin wrinkles and have completed the present disclosure.

SUMMARY

In an aspect, the present disclosure is directed to providing a composition for enhancing skin elasticity or improving skin wrinkles.

In an aspect, the present disclosure provides a composition for enhancing skin elasticity or improving skin wrinkles, which contains heptahydroxyflavan or a salt, isomer, hydrate or solvate thereof as an active ingredient.

In one another aspect, the present disclosure provides a method for enhancing skin elasticity or improving skin wrinkles, comprising administering, to a subject in need thereof, a composition containing heptahydroxyflavan or a salt, isomer, hydrate or solvate thereof as an active ingredient.

In an aspect, the heptahydroxyflavan or a salt, isomer, hydrate or solvate thereof, which is an active ingredient of the composition of the present disclosure, can enhance skin elasticity and improve skin wrinkles by inhibiting MMP-1 activity. In addition, the heptahydroxyflavan or a salt, isomer, hydrate or solvate thereof, which is an active ingredient of the composition of the present disclosure, can be used in various compositions such as cosmetics, health functional foods, etc. because it is safe with no cytotoxicity.

DETAILED DESCRIPTION

Figure 1A:
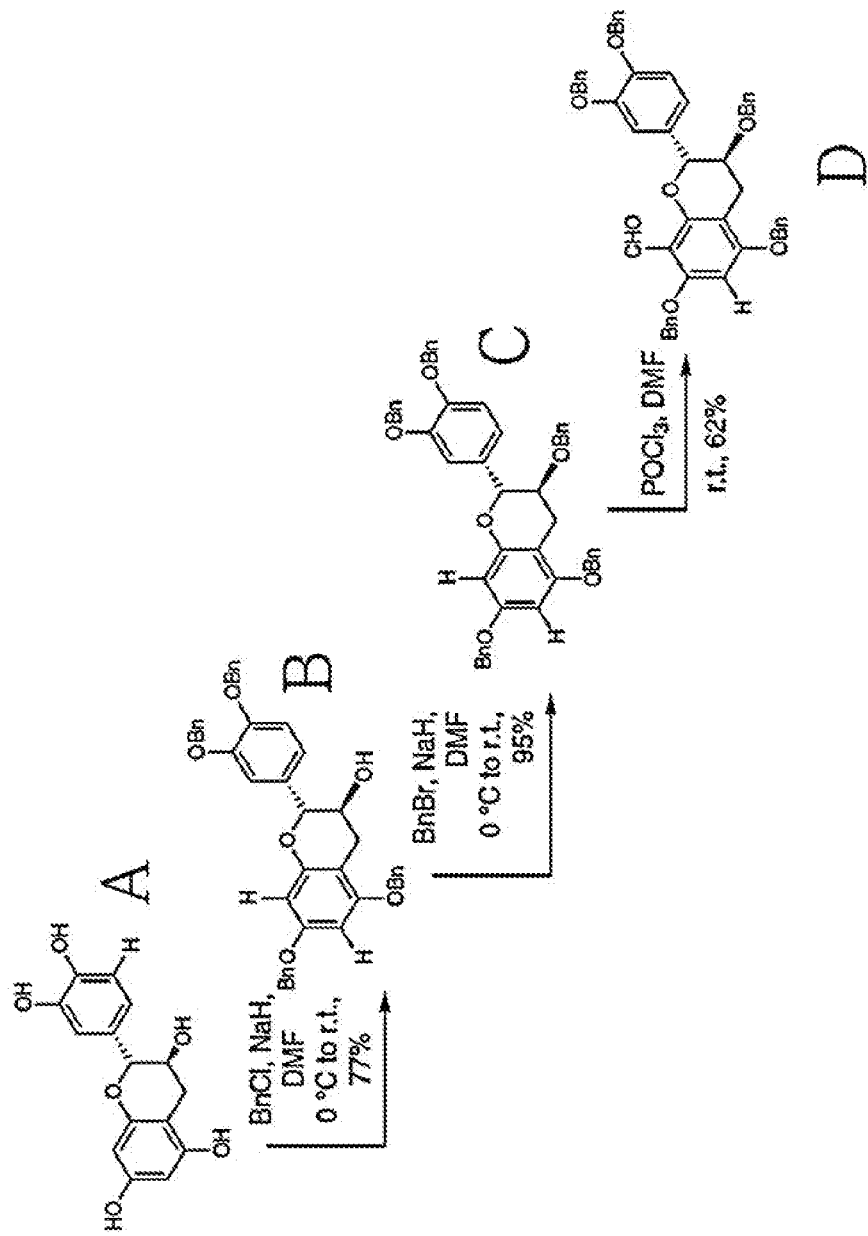
FIGS. 1A and 1B schematically describe a process of preparing heptahydroxyflavan.

In an aspect, the present disclosure provides a composition for enhancing skin elasticity or improving skin wrinkles, which contains heptahydroxyflavan or a salt, isomer, hydrate or solvate thereof as an active ingredient.

In one another aspect, the present disclosure provides a method for enhancing skin elasticity or improving skin wrinkles, comprising administering, to a subject in need thereof, a composition containing heptahydroxyflavan or a salt, isomer, hydrate or solvate thereof as an active ingredient.

Hereinafter, the present disclosure is described in detail.

In the present disclosure, the 'salt' includes any organic or inorganic addition salt derived from heptahydroxyflavan, which is used in such a concentration that exhibits relatively nontoxic and harmless effective actions to an individual, and which has side effects that do not decrease the advantageous effects of heptahydroxyflavan. It includes all the salts having acidic or basic functional groups that may be present on heptahydroxyflavan. For example, it may be an acid addition salt formed by a free acid or a metal salt formed by an acid or a base.

For example, an inorganic acid or an organic acid may be used as the free acid. As the inorganic acid, hydrochloric acid, hydrobromic acid, bromic acid, sulfuric acid, sulfurous acid, nitric acid, phosphoric acid, etc. may be used. As the organic acid, acetic acid, propionic acid, hexanoic acid, cyclopentylpropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2,2,2]-oct-2-ene-1-carboxylic acid, glucoheptonic acid, 3-phenylpropionic acid, trimethylacetic acid, tert-7butylacetic acid, lauryl sulfuric acid, gluconic acid, glutamic acid, hydroxynaphthoic acid, salicylic acid, stearic acid, muconic acid, citric acid, etc. may be used. For example, the metal salt may be an alkali metal salt or an alkaline earth metal salt.

In the present disclosure, the 'isomer' includes not only optical isomers, i.e., essentially pure enantiomers, essentially pure diastereomers or mixtures thereof, but also conformational isomers, i.e., isomers differently only in the angle of one or more chemical bonds, and position isomers. The position isomers include geometric isomers such as tautomers or cis-trans isomers. The expression 'essentially pure' means, when used, for example, with regard to enantiomers or diastereomers, that specific compounds, e.g., enantiomers or diastereomers, are present in an amount of about 90% (w/w) or more, 91% or more, 92% or more, 93% or more, 94% or more, 95% or more, 96% or more, 97% or more, 98% or more, 99% or more, or 99.5% or more.

For example, the isomer of heptahydroxyflavan may be (2R,3S)-heptahydroxyflavan represented by Chemical Formula 1 or (2R,3R)-heptahydroxyflavan represented by Chemical Formula 2, although not being limited thereto.

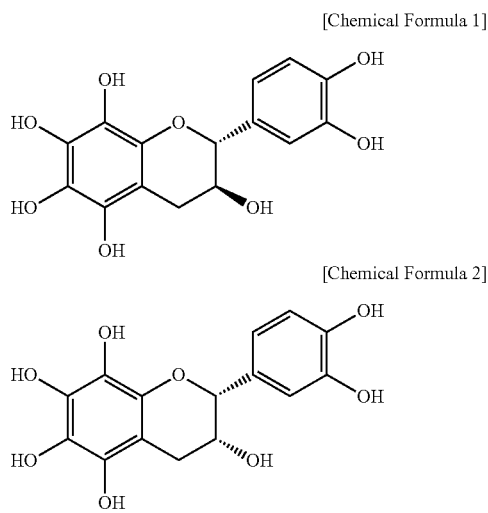

[Chemical Formula 1]

[Chemical Formula 2]

In the present disclosure, the 'hydrate' refers to a compound to which water is bound. The term is used in a broad sense, including an inclusion compound which lacks chemical bonding with water.

In the present disclosure, the 'solvate' refers to a higher-order compound formed between a molecular or ion of a solute and a molecular or ion of a solvent.

In an aspect, the heptahydroxyflavan or a salt, isomer, hydrate or solvate thereof of the present disclosure can be purchased commercially or can be obtained through synthesis, etc.

In an aspect, the administration dosage of the heptahydroxyflavan or a salt, isomer, hydrate or solvate thereof may be 0.1 mg/kg/day or more, 0.5 mg/kg/day or more, 1 mg/kg/day or more, 1.5 mg/kg/day or more, 2 mg/kg/day or more, 2.5 mg/kg/day or more, 3 mg/kg/day or more, 3.5 mg/kg/day or more, 4 mg/kg/day or more, 4.5 mg/kg/day or more, 5 mg/kg/day or more, 5.5 mg/kg/day or more, 6 mg/kg/day or more, 6.5 mg/kg/day or more, 7 mg/kg/day or more, 7.5 mg/kg/day or more, 8 mg/kg/day or more, 8.5 mg/kg/day or more, 9 mg/kg/day or more, 9.5 mg/kg/day or more, 10 mg/kg/day or more, 10.5 mg/kg/day or more, 11 mg/kg/day or more or 11.5 mg/kg/day or more, and 12 mg/kg/day or less, 12.5 mg/kg/day or less, 13 mg/kg/day or less, 13.5 mg/kg/day or less, 14 mg/kg/day or less, 14.5 mg/kg/day or less, 15 mg/kg/day or less, 15.5 mg/kg/day or less, 16 mg/kg/day or less or 16.5 mg/kg/day or less, although not being limited thereto.

In an aspect, the heptahydroxyflavan or a salt, isomer, hydrate or solvate thereof may be contained in an amount of 0.01 wt % or more, 0.03 wt % or more, 0.05 wt % or more, 0.08 wt % or more, 0.1 wt % or more, 0.3 wt % or more, 0.5 wt % or more, 0.8 wt % or more, 1 wt % or more, 1.3 wt % or more, 1.5 wt % or more, 1.8 wt % or more, 2 wt % or more, 2.3 wt % or more, 2.5 wt % or more, 2.8 wt % or more, 3 wt % or more, 3.3 wt % or more, 3.5 wt % or more, 3.8 wt % or more, 4 wt % or more, 4.3 wt % or more, 4.5 wt % or more or 4.8 wt % or more, and 5 wt % or less, 5.3 wt % or less, 5.5 wt % or less, 5.8 wt % or less, 6 wt % or less, 6.3 wt % or less, 6.5 wt % or less, 6.7 wt % or less, 7 wt % or less, 7.3 wt % or less, 7.5 wt % or less, 7.8 wt % or less, 8 wt % or less, 8.3 wt % or less, 8.5 wt % or less, 8.8 wt % or less, 9 wt % or less, 9.3 wt % or less, 9.5 wt % or less, 9.8 wt % or less and 10 wt % or less, based on the total weight of the composition, although not being limited thereto.

In an aspect, skin is composed of the epidermis, which is stratified squamous epithelium, the dermis, which is a dense connective tissue, and the subcutaneous tissue, which is a loose connective tissue. For example, the composition of the present disclosure may be particularly effective in enhancing skin elasticity or improving skin wrinkles when skin elasticity is decreased or skin wrinkles are severe due to damage to the dermis or decreased volume of the dermis.

In an aspect, the composition may inhibit MMP-1.

In an aspect, the composition may lack cytotoxicity.

In an aspect, the composition of the present disclosure may be a cosmetic composition.

In the present disclosure, the 'cosmetic composition' refers to a composition which improves the appearance of human body, and the cosmetic composition for enhancing skin elasticity or improving skin wrinkles of the present disclosure refers to a composition which improves the appearance of human body by suppressing negative effects on skin, although not being limited thereto.

In an aspect, the cosmetic composition may further contain, in addition to the heptahydroxyflavan or a salt, isomer, hydrate or solvate thereof, an adjuvant or a carrier commonly used in a cosmetic composition, such as an antioxidant, a stabilizer, a solubilizing agent, a vitamin, a pigment, a flavor, etc. For example, the cosmetic composition may further contain an auxiliary ingredient such as glycerin, butylene glycol, polyoxyethylene hydrogenated castor oil, tocopheryl acetate, citric acid, panthenol, squalane, sodium citrate, allantoin, etc.

In an aspect, the cosmetic composition may be prepared into any formulation applied onto skin, which is commonly used in the art. Examples include a solution, a suspension, an emulsion, a paste, a gel, a cream, a lotion, a powder, a soap, a surfactant-containing cleanser, an oil, a powder foundation, an emulsion foundation, a wax foundation, a spray, etc., although not being limited thereto. More specifically, it may be formulated into a softening lotion, a nourishing softening, a nourishing cream, a massage cream, an essence, an eye cream, a cleansing cream, a cleansing foam, a cleansing water, a mask pack, a spray or a powder.

In an aspect, when the formulation of the present disclosure is a paste, a cream or a gel, an animal fiber, a plant oil, a wax, paraffin, starch, tragacanth, a cellulose derivative, polyethylene glycol, silicone, bentonite, silica, talc, zinc oxide, etc. may be contained as a carrier.

In an aspect, when the formulation of the present disclosure is a powder or a spray, lactose, talc, silica, aluminum hydroxide, calcium silicate, polyamide powder, etc. may be contained as a carrier. In particular, a spray may further contain a propellant such as chlorofluorohydrocarbon, propane/butane, dimethyl ether, etc.

In an aspect, when the formulation of the present disclosure is a solution or an emulsion, a solvent, a solubilizing agent, an emulsifier, etc. may be contained as a carrier. Specifically, water, ethanol, isopropanol, ethyl carbonate, ethyl acetate, benzyl alcohol, benzyl benzoate, propylene glycol, 1,3-butylene glycol, glycerol aliphatic ester, polyethylene glycol, fatty acid ester of sorbitan, etc. may be contained as a carrier.

In an aspect, when the formulation of the present disclosure is a suspension, a liquid diluent such as water, ethanol, propylene glycol, etc., a suspending agent such as ethoxylated isostearyl alcohol, polyoxyethylene sorbitol ester, polyoxyethylene sorbitan ester, etc., microcrystalline cellulose, aluminum metahydroxide, bentonite, agar, tragacanth, etc. may be contained as a carrier.

In an aspect, when the formulation of the present disclosure is a surfactant-containing cleanser, an aliphatic alcohol sulfate, an aliphatic alcohol ether sulfate, sulfosuccinic acid monoester, isethionate, an imidazolinium derivative, methyl taurate, sarcosinate, a fatty acid amide ether sulfate, amidoalkyl betaine, an aliphatic alcohol, a fatty acid glyceride, a fatty acid diethanolamide, a vegetable oil, a lanolin derivative, ethoxylated glycerol fatty acid ester, etc. may be contained as a carrier.

In an aspect, the composition of the present disclosure may be a health functional food composition.

In the present disclosure, the 'health functional food composition' refers to a food imparted with a specific function by physical, biochemical or biotechnical techniques, or a processed food designed to impart regulatory functions regarding control of biological defense rhythms, prevention of and recovery from diseases, etc., which is harmless to the human body even after long-term use.

In an aspect, the health functional food may contain a sitologically acceptable food additive, and may further contain an adequate carrier, excipient or diluent commonly used for preparation of health functional food.

In an aspect, the health functional food composition may be used as a food additive. In this case, the composition may be added either alone or in combination with another food or food ingredient according to common methods. The mixing amount of the active ingredient may be determined adequately depending on purpose of use (prevention, health improvement or treatment).

In an aspect, the health functional food may be, for example, a dairy product including ice cream, a soup, a beverage, a tea, a drink, an alcoholic beverage, a multivitamin, etc., and includes a food imparted with a specific function or a processed food designed to impart regulatory functions regarding control of biological defense rhythms, prevention of and recovery from diseases, etc.

In an aspect, the health functional food composition may further contain various nutrients, vitamins, electrolytes, flavors, colorants, pectic acid and salts thereof, alginic acid and salts thereof, organic acids, protective colloidal extenders, pH control agents, stabilizers, antiseptics, glycerin, alcohols, carbonating agents used in carbonated beverages, etc.

In the foregoing description, the same contents described above were omitted to avoid redundancy, and the terms not defined in the present disclosure have the meanings commonly used in the art to which the present disclosure belongs. In addition, unless clearly stated otherwise, the expression 'or' is to be understood to include 'and'.

Hereinafter, the present disclosure will be described in detail through examples, test examples and formulation examples. However, the following examples, test examples and formulation examples are for illustrative purposes only and it will be apparent to those of ordinary skill in the art that the scope of the present disclosure is not limited by the examples, test examples and formulation examples. The examples, test examples and formulation examples of the present disclosure are provided to more fully describe the present disclosure to those of ordinary skill in the art.

Example 1. Heptahydroxyflavan

As shown in FIG. 1A, tetra-O-benzylcatechin (B) and penta-O-benzylcatechin (C) were prepared continuously from catechin (A), which was a starting material, in the presence of NaH, BnCl/BnBr and DMF. Then, compound D, which is a position isomer (regioisomer) of the penta-O-benzylcatechin (C), was prepared via the Vilsmeier-Haack reaction. Then, compound E was prepared by introducing a new hydroxyl group at the C-6 position of the compound D in a DMDO solvent at −40° C.

Figure 1B:
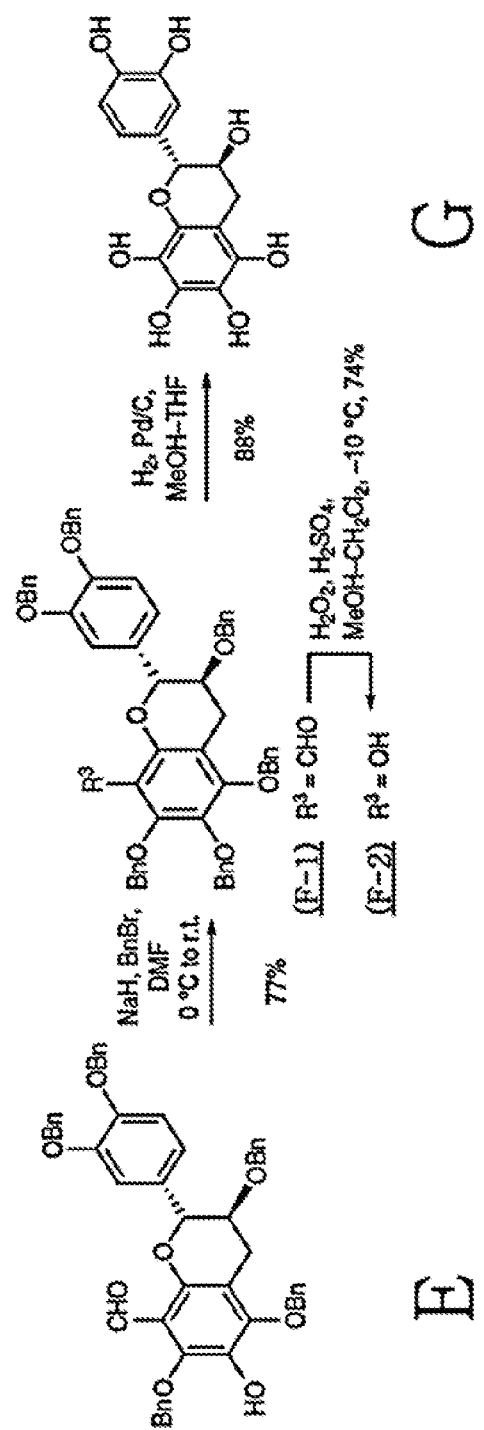

Then, as shown in FIG. 1B, after capping the hydroxyl group at the C-6 position of the compound E with a protecting group by treating with NaH, BnBr and DMF, compound F-1 was prepared via the Darkin reaction. Subsequently, after obtaining compound F-2 by conducting reaction slowly, (2R,3S)-heptahydroxyflavan represented by Chemical Formula 1 was obtained by hydrogenating all the benzyl groups.

[Chemical Formula 1]

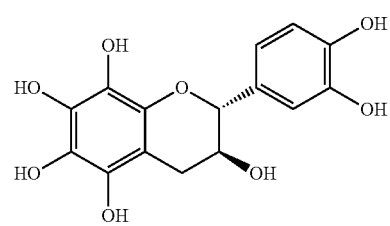

(2R,3R)-Heptahydroxyflavan represented by Chemical Formula 2 was obtained through the same procedure described above, except for using epicatechin instead of catechin as the starting material.

[Chemical Formula 2]

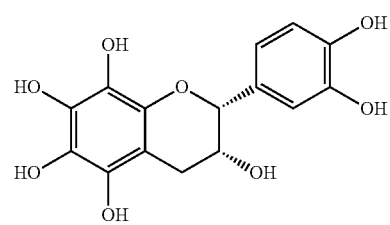

Test Example 1. Cytotoxicity Test

Normal human dermal fibroblasts acquired from ATCC were cultured in a medium containing FBS for 24 hours under the condition of 37° C. and 5% $CO_2$. After replacing the medium with a serum-free medium, the cells were cultured for 24 hours or longer. The (2R,3S)-heptahydroxyflavan (hereinafter, also referred to as 'APNP-054') and (2R,3R)-heptahydroxyflavan (hereinafter, also referred to as 'APNP-055') obtained in Example 1 were dissolved in 100% DMSO to prepare a total of 10 samples at concentrations of 6.25 μg/mL (=about 19.4 μM), 12.5 μg/mL (=about 38.3 μM), 25 μg/mL (=about 77.6 μM), 50 μg/mL (=about 155.1 μM) and 100 μg/mL (=about 310.3 μM), respectively. As comparative examples, catechin and epicatechin were dissolved in 100% DMSO to prepare a total of 10 samples at concentrations of 6.25 μM, 12.5 μM, 25 μM, 50 μM and 100 μM, respectively. Then, after seeding the human fibroblasts onto a 96-well plate with $0.6 \times 10^4$ cells/well, they were stabilized for 24 hours under the condition of 37° C. and 5% $CO_2$, and then treated with the 20 samples. A negative control group was treated with none of the above samples. 24 hours later, MTT assay was conducted according to a commonly employed method. The result is shown in FIG. 2.

Figure 2:
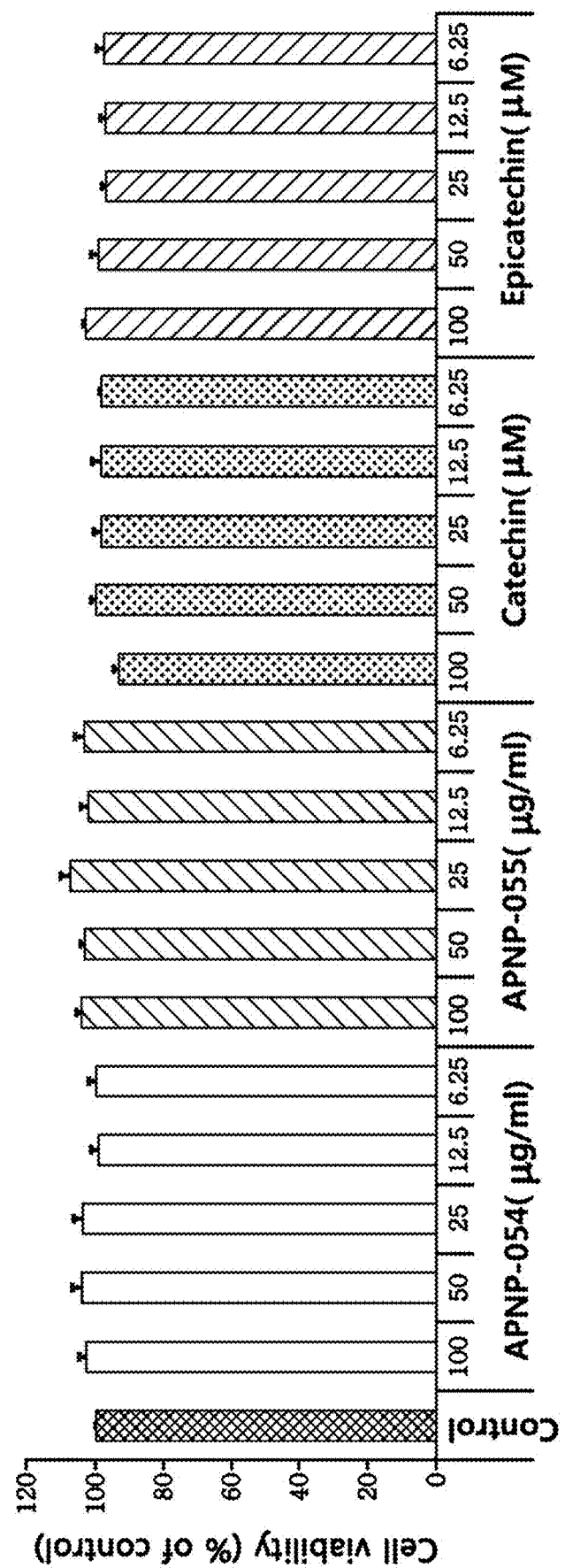
FIG. 2 shows a result of investigating cytotoxicity.

As seen from FIG. 2, the heptahydroxyflavan of the present disclosure showed no cytotoxicity even at high concentrations. This means that the heptahydroxyflavan of the present disclosure is a safe substance that can be treated to the human body in various forms such as cosmetics, medicine, food, etc.

Test Example 2. Investigation of Effect on Skin Wrinkles or Skin Elasticity

Keratinocytes (HaCaT cells) acquired from ATCC were seeded onto a 6-well plate with $2.5 \times 10^5$ cells/well and cultured for 24 hours under the condition of 37° C. and 5% $CO_2$. Then, after replacing the medium with an FBS-free DMEM medium to starve the cells, they were treated with UV on the next day.

Separately from this, human fibroblasts acquired from ATCC were seeded onto a 96-well plate with $0.6 \times 10^4$ cells/well and cultured for 24 hours under the condition of 37° C. and 5% $CO_2$. Then, the cells were starved by replacing the medium with an FBM medium with no supplement. Then, the UV-stimulated HaCaT cell culture and the human fibroblast culture were treated with a total of 6 samples prepared by dissolving the (2R,3S)-heptahydroxyflavan and (2R,3R)-heptahydroxyflavan obtained in Example 1 in 5% DMSO to concentrations of 5 μg/mL (=about 15.5 μM), 10 μg/mL (=about 31.0 μM) and 20 μg/mL (=about 62.1 μM), respectively. As comparative examples, the cultures were treated with a total of 6 samples prepared by dissolving catechin and epicatechin in 5% DMSO at concentrations of 25 μM, 50 μM and 100 μM, respectively.

After the treatment with the samples, the expression level of MMP-1 was measured using the MMP-1 ELISA kit (R&D Systems). Separately from this, positive control groups were treated with 10 μM EGCG or 10 μM retinoic acid instead of heptahydroxyflavan in the same manner as described above. The result is shown in Table 1 and FIG. 3.

TABLE 1

|   |   | MMP-1 production |
|---|---|---|
| Control |   | 100 |
| UV |   | 260.4 |
| EGCG (μM) | 10 | 115.4 |
| RA (μM) | 10 | 104.5 |
| APNP-054 (μg/mL) | 20 | 183.2 |
|   | 10 | 267.7 |
|   | 5 | 282.1 |
| APNP-055 (μg/mL) | 20 | 160.6 |
|   | 10 | 286.6 |
|   | 5 | 281.0 |

TABLE 1-continued

|   |   | MMP-1 production |
|---|---|---|
| Catechin (μM) | 100 | 257.3 |
|   | 50 | 287.4 |
|   | 25 | 308.2 |
| Epicatechin (μM) | 100 | 196.2 |
|   | 50 | 289.1 |
|   | 25 | 294.8 |

Figure 3:
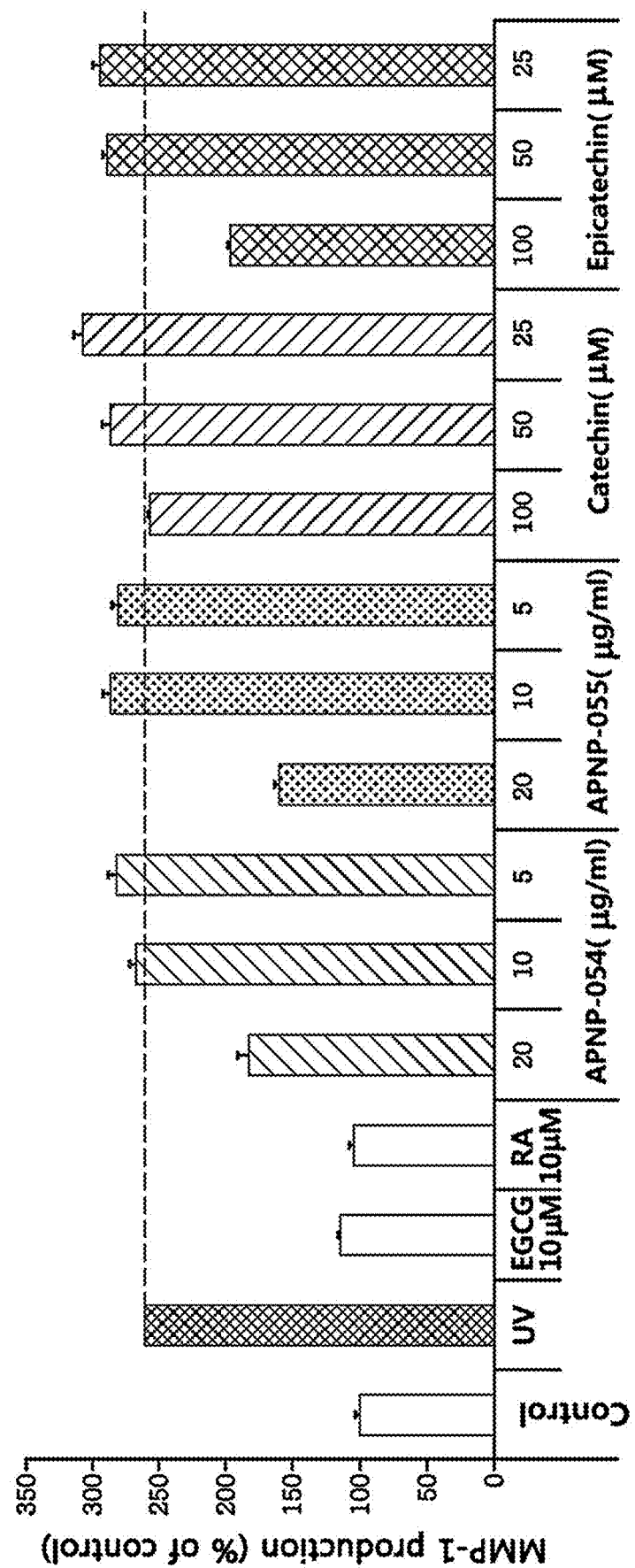
FIG. 3 shows a result of investigating the effect of MMP-1 expression level on skin wrinkles or skin elasticity.

As seen from Table 1 and FIG. 3, heptahydroxyflavan (APNP-054: (2R, 3S)-heptahydroxyflavan, APNP-055: (2R, 3R)-heptahydroxyflavan) exhibits remarkably superior effect of inhibiting MMP-1 as compared to catechin or epicatechin having similar chemical structure. This means that heptahydroxyflavan has superior effect of enhancing skin elasticity or improving skin wrinkles as compared to other compounds having similar chemical structure.

Formulation Example 1. Preparation of Cosmetic Formulations 1-1. Preparation of Softening Lotion A softening lotion was prepared according to a common method by mixing 0.1 wt % of heptahydroxyflavan, 5.2 wt % of 1,3-butylene glycol, 1.5 wt % of oleyl alcohol, 3.2 wt % of ethanol, 3.2 wt % of polysorbate 20, 2.0 wt % of benzophenone-9, 1.0 wt % of carboxyvinyl polymer, 3.5 wt % of glycerin, a trace amount of flavor, a trace amount of antiseptic, and purified water as the balance.

1-2. Preparation of Milk Lotion

A milk lotion was prepared according to a common method by mixing 0.1 wt % of heptahydroxyflavan, 5.1 wt % of glycerin, 4.2 wt % of propylene glycol, 3.0 wt % of tocopheryl acetate, 4.6 wt % of liquid paraffin, 1.0 wt % of triethanolamine, 3.1 wt % of squalane, 2.5 wt % of macadamia nut oil, 1.6 wt % of polysorbate 60, 1.6 wt % of sorbitan sesquioleate, 0.6 wt % of propylparaben, 1.5 wt % of carboxyvinyl polymer, a trace amount of flavor, a trace amount of antiseptic, and purified water as the balance.

1-3. Preparation of Nourishing Cream

A nourishing cream was prepared according to a common method by mixing 0.5 wt % of heptahydroxyflavan, 4.0 wt % of glycerin, 3.5 wt % of vaseline, 2.1 wt % of triethanolamine, 5.3 wt % of liquid paraffin, 3.0 wt % of squalane, 2.6 wt % of beeswax, 5.4 wt % of tocopheryl acetate, 3.2 wt % of polysorbate 60, 1.0 wt % of carboxyvinyl polymer, 3.1 wt % of sorbitan sesquioleate, a trace amount of flavor, a trace amount of antiseptic, and purified water as the balance.

Formulation Example 2. Preparation of Food Formulations 2-1. Preparation of Health Food After preparing a granule by mixing 100 mg of heptahydroxyflavan, an adequate amount of vitamin mixture, 70 g of vitamin A acetate, 1.0 mg of vitamin E, 0.13 mg of vitamin $B_1$, 0.15 mg of vitamin $B_2$, 0.5 mg of vitamin $B_6$, 0.2 g of vitamin $B_{12}$, 10 mg of vitamin C, 10 g of biotin, 1.7 mg of nicotinamide, 50 g of folic acid, 0.5 mg of calcium pantothenate, an adequate amount of mineral mixture, 1.75 mg of ferrous sulfate, 0.82 mg of zinc oxide, 25.3 mg of magnesium carbonate, 15 mg of monopotassium phosphate, 55 mg of dicalcium phosphate, 90 mg of potassium citrate, 100 mg of calcium carbonate and 24.8 mg of magnesium chloride, a health food was prepared according to a common method.

2-2. Preparation of Health Drink

According to a common method for preparing a health drink, after mixing 100 mg of heptahydroxyflavan, 15 g of vitamin C, 100 g of vitamin E (powder), 19.75 g of iron lactate, 3.5 g of zinc oxide, 3.5 g of nicotinamide, 0.2 g of vitamin A, 0.25 g of vitamin $B_1$, 0.3 g of vitamin $B_2$ and an adequate amount of water, the resulting solution was heated at 85° C. for about 1 hour under stirring. The prepared solution was filtered, filled in a sterilized 2-L container and then sterilized. The prepared health drink was stored in a refrigerator.

What is claimed is:

1. A method for enhancing skin elasticity or improving skin wrinkles, comprising administering, to a subject in need thereof, a composition comprising (2R,3S)-heptahydroxyflavan or a salt, hydrate or solvate thereof as an active ingredient,
    wherein the (2R,3S)-heptahydroxyflavan or a salt, hydrate or solvate thereof is comprised in an amount of 0.01-10 wt % based on the total weight of the composition.

2. The method according to claim 1, wherein the administration dosage of the (2R,3S)-heptahydroxyflavan or a salt, hydrate or solvate thereof is 0.1-16.5 mg/kg/day.

3. The method according to claim 1, wherein the composition inhibits MMP-1.

4. The method according to claim 1, wherein the composition lacks cytotoxicity.

5. The method according to claim 1, wherein the composition is a cosmetic composition.

6. The method according to claim 1, wherein the composition is a health functional food composition.

* * * * *